United States Patent [19]

Wohler, Jr.

[11] 4,167,560

[45] Sep. 11, 1979

[54] POLYVALENT SHIPPING FEVER VACCINE

[75] Inventor: Wilson H. Wohler, Jr., San Angelo, Tex.

[73] Assignee: Texas Vet Lab, Inc., San Angelo, Tex.

[21] Appl. No.: 786,940

[22] Filed: Apr. 12, 1977

[51] Int. Cl.² .............................................. A61K 39/02
[52] U.S. Cl. ....................................................... 424/92
[58] Field of Search .................................... 424/88–92

[56] References Cited

U.S. PATENT DOCUMENTS

| | | | |
|---|---|---|---|
| 3,149,036 | 9/1964 | Woodhour et al. | 424/89 |
| 3,492,399 | 1/1970 | Prigal | 424/91 |
| 3,501,770 | 3/1970 | Gale et al. | 424/89 |
| 3,678,149 | 7/1972 | Prigal | 424/8 |
| 3,983,228 | 9/1976 | Woodhour et al. | 424/89 |

*Primary Examiner*—Shep K. Rose
*Attorney, Agent, or Firm*—Clarence A. O'Brien; Harvey B. Jacobson

[57] ABSTRACT

Veterinary compositions of matter useful as vaccines in the biologic treatment of a multifaceted livestock disease syndrome which is commonly referred to as "shipping fever", the present compositions of matter include the killed bacteria associated with the cause of the disease syndrome preferably in a water/oil emulsion. The invention further provides a method for the prophylactic and therapeutic treatment of the shipping fever disease syndrome with the aforesaid compositions of matter.

4 Claims, No Drawings

POLYVALENT SHIPPING FEVER VACCINE

BACKGROUND OF THE INVENTION

1. Field of the Invention

The invention generally relates to prophylactic and therapeutic compositions of matter and methods for administering said composition to living organisms, particularly livestock, such as cattle and sheep. The several embodiments of the invention allow protection of such livestock against microorganism attack encountered in a disease syndrome commonly known as shipping fever.

2. Description of the Prior Art

A multifaceted disease syndrome usually associated with the transportation, concentration, and confinement of animals, such as cattle, sheep, horses, similar wild species, and the like, is commonly known as shipping fever. This disease syndrome, which annually costs cattle producers million of dollars in the United States alone, is most commonly encountered in stocker and feeder cattle and sheep which have been recently weaned, transported to market, sorted and sold, and again transported to a new home, such as a farm, ranch, or feed lot. The disease can even occur in the absence of transportation or other stressful circumstances. Accordingly, while the stress adaptation response can be a significant and predisposing factor in the development of shipping fever, certain microorganism pathogens can, under conditions of adequate exposure, cause the diverse facets of the disease complex independent of the stress adaptation response.

Treatment of the bacterial phase of shipping fever in livestock has previously involved one or more of the following modalities. Firstly, aqueous bacterins containing a particular species of the bacteria associated with the syndrome either with or without an absorption delaying adjuvant, such as aluminum hydroxide, have been used. These simple aqueous bacterins have failed to induce sufficient resistance to be of value, especially within the time periods required by usual management practices common in the livestock industry. Secondly, water in mineral oil emulsion vaccines have been used against *Pasteurella multocida* infections in water buffalo and cattle. Use of this single pathogen vaccine does not provide the broad spectrum of biologic resistance required for prevention of the shipping fever complex as experienced in the North American livestock industry. Thirdly, prophylactic use of antibiotics and sulfonamides by feed, water, or individual administration has met with only limited success due to the tendency of bacteria to become resistant to antibiotic and chemotherapeutic agents. The widespread use of such agents has led to the development of resistant bacterial strains which multiply vigorously in the absence of normal competitor organisms whose populations have been reduced by widespread and sometimes injudicious use of antibiotic and chemotherapeutic agents.

Prior water in oil adjuvant bacterins have not contained the multiplicity of bacterial species required, as now taught by the present invention, to induce the broad spectrum of immune response necessitated by this complex disease syndrome. As a result, the health and productive efficiency of stocker and feeder livestock has deteriorated due to the lack of efficient broad spectrum antimicrobial biologics and to the widespread and often injudicious use of antibiotic and chemotherapeutic agents. Accordingly, even though killed bacterial vaccines have previously been available for individual treatment of a particular disease effect caused by an identifiable bacteria and even though antibiotics and chemotherapeutic agents have long been available, costly losses of cattle still occur due to the shipping fever complex which are directly attributable to the bacteria associated with the syndrome.

SUMMARY OF THE INVENTION

The present invention provides a biologic treatment modality to veterinary practitioners and livestock producers for the prophylactic and therapeutic treatment of the shipping fever disease syndrome, the resistance of treated animals to the pathogenic bacteria associated with the syndrome being markedly increased. In the shipping fever syndrome of cattle both viral and bacterial agents, individually or in combination, may be causative; however, it is the bacterial agents which are significantly more responsible for the pathology of the syndrome rather than the viral agents. In a like manner, the bacterial agents are more responsible for the greater portion of the morbidity and mortality associated with the syndrome than are the viral agents. The bacterial agents of greatest clinical significance in cattle are of the genus Pasteurella, the genus Salmonella, and enterotoxic Coliforms. Depending on the organisms present, the health of the animal, and other factors, symptoms of septicemia, pneumonia, enteritis, and panophthalmitis can occur individually or in combination. The nomenclature relative to the shipping fever complex refers to various aspects of the disease such as the organ system involved, the specific pathogen causing the disease, or the definitive pathology. Typical of the names commonly used are Hemorrhagic Septicemia, Shipping Fever, Shipping Fever Diarrhea, Pasteurellosis, Pasteurella Pneumonia, Salmonellosis, Colibacillosis, and Shipping Fever Pink Eye.

The present invention particularly provides methodology and compositions of matter for the prevention and treatment of the full scope of the disease syndrome in livestock as caused by bacteria, including the provision of protection against certain of the specific disease entities involved. Particularly, the present vaccines are comprised of the killed bacteria which, when alive and hosted by the animal under appropriate circumstances, would be capable of causing the various specific disease entities that constitute either individually or in combination the bacterial phase of the shipping fever syndrome. According to the invention, multiple species of the appropriate bacteria are propagated in pure culture, then killed and prepared as an aqueous suspension of known concentration. The aqueous suspension of killed bacteria is then preferably emulsified in an oil which may be of mineral origin, vegetable origin, or a combination thereof. The finished vaccine is injected subcutaneously in the cervical region of animals which are to be treated, the vaccine being administered prior to exposure, during incubation, or during the symtomatic phase of the disease. The vaccine is administered in the neck region to maximize entrance into the lymph drainage.

Accordingly, it is an object of the invention to provide a method and composition of matter for the biologic treatment, both prophylactic and therapeutic, of the shipping fever syndrome in livestock.

It is a further object of the invention to provide a killed bacteria vaccine comprised of at least the most clinically significant bacterial agents associated with shipping fever syndrome in livestock, the killed bacteria being preferably suspended in a water/oil emulsion.

It is another object of the invention to provide a method and a composition of matter for the prevention and treatment of bacterial infections associated with shipping fever, Pasteurellosis, Salmonellosis, Colibacillosis, pneumonia, and enteritis of mixed bacterial origin in livestock and other animals through the use of a water in oil emulsion adjuvant polyvalent vaccine containing the killed form of bacterial agents causative thereof.

It is yet another object of the invention to reduce the severity of viral infections associated with shipping fever in cattle and other animals through the induction of interferon by administration of a polyvalent water in oil emulsion vaccine containing the killed form of bacterial agents causative thereof.

DESCRIPTION OF THE PREFERRED EMBODIMENTS

The symptoms associated with shipping fever in livestock are primarily caused by bacterial agents, certain viral agents being also involved in certain species of livestock. In cattle, viral agents having a pathological effect include Infectious Bovine Rhinotracheitis, Bovine Virus Diarrhea, and Parainfluenza 3 Viruses. The bacterial agents responsible for the greater amount of the pathology of shipping fever in cattle and which commonly are of greater etiologic significance include *Pasteurella hemolytica, Pasteurella multocida,* and *Salmonella typhimurium.* Other bacterial agents, such as other species of Salmonella and organisms such as *Escherichia coli, Arizona arizonae, Pseudomonas aeruginosa, Corynebacterium pyogenes, Proteus vulgaris, Streptococci, Staphylococci, Morexella bovis,* and undoubtedly others not yet defined, can also be of pathogenic importance in this multifaceted disease syndrome. However, Pasteurella, Salmonella, and enterotoxic coliform organisms are most frequently the bacterial agents of greatest clinical significance. These organisms may produce disease individually or in combination, and associated or not associated with shipping, concentration, confinement, and inclement weather, although these conditions and circumstances are more frequently and commonly associated with shipping fever.

Polyvalent vaccines according to the invention which are most useful in the treatment of cattle contain *Pasteurella hemolytica* and *Pasteurella maltocida,* the vaccine further containing *Salmonella typhimurium* and/or *Escherichia coli.* A polyvalent vaccine containing these four bacterins is especially useful.

In feeder sheep and lambs the circumstances surrounding the onset of shipping fever are similar to those associated with bovine shipping fever. At present, however, no viral agents have been recognized as occurring in ovine shipping fever. The commonly involved bacterial agents producing the disease syndrome in sheep are *Pasteurella multocida, Salmonella typhimurium,* enterotoxic *Escherichia coli,* and *Pseudomonas aeruginosa.* The present vaccines, particularly when used in the treatment of sheep, can be prepared without the use of the adjuvant. In the treatment of sheep, the shorter marketing cycle and concerns relative to tissue damage and residue at the time of slaughter are factors in the use of the present vaccines in an aqueous solution. While the present vaccines provide stronger and more prolonged immunity when used as a water in oil emulsion, the present compositions of matter are therapeutically useful as aqueous bacterin combinations. As a particular example, a combination of the killed bacteria indicated above as used in the treatment of sheep was administered in aqueous solution to 41,600 head of lambs, death losses falling as a result of this treatment from a usual level of 5% to under 1.5%. The concentration ranges of each bacterin in the aqueous vaccine varied from $10^8$ to $10^{10}$ per dosage in the manner of the exact preparation referred to hereinafter relative to the preparation of a bovine shipping fever vaccine.

In the practice of the present method and in the use of the present compositions of matter, livestock and other animals can be protected against certain specific disease entities which constitute the principle facets of the shipping fever complex, the invention providing a biologic treatment modality independent of the use of antibiotic or chemotherapeutic agents. The modus operandi is primarily antibacterial, however retardation of virus replication is accomplished through the induction of interferon. In those species of livestock not known to be subject to the viral phase of shipping fever, protection against bacterial agents is intentionally provided while protection against viral agents is inherent in the present treatment as will be understood. The treatment provided by the present invention is economical, safe, and easily practiced, the invention being capable of preventing a substantial portion of the economic loss attributable to the specific and non-specific disease entities which individually and in various combinations constitute the multiple facets of shipping fever.

The invention provides compositions of matter, known in the art as vaccines, which comprise the killed bacteria that, when alive and under appropriate circumstances, would be capable of causing the various specific disease entities which individually or in combination constitute the bacterial aspect of the shipping fever syndrome. A particular vaccine can be prepared for each livestock species, the multiple species of bacteria responsible for the disease syndrome in a particular livestock species being propagated in pure culture, then killed and prepared as an aqueous suspension of known concentration. A vaccine can also be prepared from the major bacterial agents known to be associated with the syndrome in a given livestock species or in a given outbreak of the syndrome. When indicated to the practitioner, a vaccine can be prepared which contains killed bacteria of a number of selected species. The aqueous suspension of the killed bacteria is preferably emulsified in a mineral oil, a vegetable oil, or a combination of the two types of oils, emulsification being accomplished by techniques well known in the art. The water/oil emulsion, or finished vaccine, can then be injected subcutaneously in the cervical region of livestock either prior or subsequently to exposure to the etiologic agents of shipping fever. The present vaccines can be administered prior to or during the incubation period or during the symptomatic phase of the disease, in all instances to the benefit of the animal. The vaccines are to be administered subcutaneously in the neck region for the purpose of maximizing entrance into the lympatic system.

The unusually beneficial effects of the present compositions of matter are believed to be attributable to several specific factors. Firstly, the antigenic response to a bacterin prepared as a water in oil emulsion is more rapid and of greater magnitude than a similar bacterin prepared as an aqueous suspension. Secondly, in the practice of the invention, large numbers of gram negative bacteria injected in the vaccine cause the cells of the livestock to produce an antiviral protein known as interferon, the induced interferon response increasing the natural interferon response of the animal to control any concurrent viral infection. Thirdly, the shipping fever disease complex frequently involves the pathogenic activity of more than one infectious agent. Increased susceptibility to pathogenic activity is caused by stress. When a microorganism infects an animal and causes disease it also causes a "disease response stress" in the animal, which stress renders the animal more susceptible to a second, and perhaps less pathogenic, organism, a succession of microbially induced stresses and attack by successive pathogenic organisms then being possible. The weakened condition of the livestock, due to the effects of weaning, shipping, crowding, sorting, changes of feed, water, or weather, renders the animal more susceptible to the entrance into the body of the first pathogen and to additional bacterial pathogens. The first pathogen entering the animal then further weakens said animal and causes greater susceptibility to subsequent attack of infectious organisms. By providing a multiplicity of antigens in a vaccine according to the present invention, not only is the danger of disease caused by primary specific pathogens reduced, but the possibility of microbially induced stress which would occur as a result of infection by any specific disease pathogen is also reduced. Thus, the possibility of other, and perhaps less pathogenic, bacteria or other infectious agents having the capability to cause disease in the animal is reduced.

The present vaccines further act to activate macrophages to increased phagocytic activity. The antigens of the vaccines are released from within the droplets of oil as the oil is removed by phagocytic cells. A more sustained antigenic action thus occurs than if the antigens were contained in a simple aqueous or normal saline solution. The water in oil emulsion also attracts both antibody producing cells and mononuclear phagocytes to the site of the injection, assistance in the efficient uptake of the antigen and its utilization by the ultimate target cells being thereby provided. In addition to the sustained release of the antigen-adjuvant complex, the antigen is more effectively disseminated via the lymphatics to the prime antibody forming tissues, a rapid and efficient antibody response thereby resulting. After a single subcutaneous injection in the neck region, antibody formation can be detected within hours and can continue for many months.

In addition to the increase resistance to the specific diseases due to antibody formation provided by the present vaccines, the present adjuvant vaccines also stimulate the cellular immunity of the animal. With many species of infectious microorganisms, the level of specific antibody circulating in the animal does not significantly alter the final outcome of the disease, this being particularly true of facultative intracellular parasites, such as *Salmonella, Mycobacteria, Brucella,* and *Listeria.* Many of the leucocyts and somatic cells of the body will contain the infectious agents and are almost impervious to antibodies and even antibiotics. Lymphocytes exposed to the bacterial antigens in this adjuvant bacterin become sensitized and release mediators (lymphokines) which convert normal macrophages into activated macrophages. In this state, the macrophages have elevated enzyme levels and are now able to engulf and kill almost all pathogenic bacteria they encounter including the facultative intracellular parasites. Therefore, the present adjuvant vaccine increases resistance to many bacterial diseases in a non-specific manner. The present water in oil emulsion adjuvant killed bacterial vaccines can thus be used as a therapeutic biological in cases where the animal is already infected with a bacterial agent.

An additional effect which occurs with subcutaneous injections of this adjuvant vaccine is the induction of interferon. The injection of gram negative bacteria, including *Escherichia coli,* induces interferon, thereby resulting in an increased resistance to viral infections in a non-specific manner. The inclusion of the gram negative bacteria in the adjuvant vaccine results in the more efficient transport of bacterial cells to interferon producing organs such as the spleen. The present water in oil emulsion adjuvant killed specific bacterial vaccines efficiently act both to prevent and treat shipping fever and the specific diseases which are operative in the complex disease syndrome, the vaccines providing effects which are both specific and non-specific responses to the antigens contained in the vaccines. The induced responses are more rapid, of a higher level, and of greater duration than would be the case if the antigens were prepared as a simple aqueous bacterin.

From the foregoing, it can be seen that the non-specific effects of the present vaccines can at least be attributed to (1) the induction of interferon production by the cells of the animal, either additionally to natural interferon induction caused by the presence of viral entities or originally when viral entities are not present or not yet present in the animal; (2) the stimulation of phagocytosis by macrophages; and, (3) disease-induced stress reduction by specific disease prevention.

Preparation of a particular vaccine according to the invention is now described, the vaccine being particularly useful for treatment of bovine shipping fever. It is to be understood, however, that species of microorganisms other than those used in the following specific formulation can be utilized in the practice of the present invention. Further, species of microorganisms additional to those expressly named in the following formulation can be used. In a like manner, a vaccine according to the invention can be formulated with only a portion of the species of microorganisms expressly named in the following formulation. It is also to be understood that no specific concentration of killed microorganisms in the aqueous suspension from which the final vaccine is made or in the final vaccine is expressly called for by the invention. Since such concentrations can vary greatly in practice due to a number of factors, such as animal body weight, the circumstances of the treatment, etc., it is within the scope of the invention to indicate that an effective amount of the vacvine be used, the concentration of the killed microorganisms varying in the vaccine to provide an effective amount in any given treatment situation. The use of the present vaccines are also not limited to cattle and sheep, it being understood that for all animal species treated, a certain bacterial population exists which can be generally associated with the disease syndrome. The vaccine needed for treatment of the disease syndrome in any given animal species can be prepared from the full bacterial population or from a chosen portion of the population. The choice is typically dependent on circumstances peculiar to a particular treatment situation or to the necessity or desirability for advance preparation of the vaccines. An effective amount of the present vaccines is taken to comprise a dosage containing at least $1 \times 10^8$ cells of all bacteria species, larger concentrations per dosage being also useful with $1 \times 10^{10}$ cells per dosage being typically utilized. The species population in such dosages are essentially equalized but can vary within the scope of the invention.

The present vaccines include a multiplicity of killed specific bacterial pathogens infective for the various organ systems involved in shipping fever of the host animal species which is to be treated, the numbers of the bacterial pathogens being sufficient to elicit a full prophylactic and therapeutic response. Further, the present vaccines include these killed bacteria in suspension in the aqueous phase of a water in oil emulsion.

As an example of the invention, the following describes the preparation of a particular polyvalent water in oil emulsion adjuvant killed bacteria bovine shipping fever vaccine:

I. Organisms Used in the Preparation of the Exemplary Vaccine:

| | |
|---|---|
| Pasteurella multocida | Paracolon species |
| pasteurella hemolytica | Proteus vulgaris |
| Salmonella typhimurium | Pseudomonas aeruginosa |
| Escherichia coli | Morexella bovis |

II. Production Steps Employed in the Preparation of the Exemplary Vaccine:

(A) Organism Preparation

Pure cultures of each species of organism are individually grown on 5% sheep cell blood agar plates for 48 hours at 37 degrees C. Cultures are examined grossly and microscopically for purity. Cells are harvested by washing from the surface of the blood agar with distilled water. A sample can be then removed for viable cell count determination. The remaining cell suspension is heated to 60 degrees C. for 30 minutes and is then allowed to cool. The cell suspension is tested for sterility by plating on blood agar and incubating at 37 degrees C. for 48 hours. The killed cell suspension is adjusted to a concentration of $1 \times 10^{11}$ per milliliter. Formaldehyde solution is added to yield a concentration of 2% formaldehyde. The resulting formalized, killed cell suspension contains $1 \times 10^{11}$ cells per milliliter and constitutes the formalized Stock Cell Suspension. The Stock Cell Suspensions are stored at 5 degrees C.

(B) Adjuvant Preparation

One hundred milliliters of water in oil emulsifying agent is mixed with 900 milliliters of NF Light Mineral Oil and sterilized by autoclaving at 121 degrees C. for 15 minutes.

(C) Fabrication of Finished Bacterin

Ten milliliter samples of each sterile formalized Stock Cell Suspension are added to 920 milliliter volumes of sterile formalized (0.14%) distilled water to give a preferred final cell concentration of $1 \times 10^9$ of each genera of organism, thereby providing a Final Cell Suspension containing 0.3% formalin. Equal volumes of the sterile Adjuvant and sterile Final Cell Suspension are blended together by conventional means to form a stable water in oil emulsion. The finished bacterin can then be bottled and check tested for sterility. Although the concentration range of each genus of bacteria included in the present vaccines is intended to be an effective amount thereof, the usual concentration range includes $10^8$ to $10^{10}$ of each genus in the Final Cell Suspension as described.

The efficacy and safety of the invention when used in the treatment of bovine shipping fever is demonstrated by the following example. The vaccine utilized was prepared as described hereinabove. Fifty head of 315 pound steers of mixed breeding were purchased in an auction market in Texas and transported 250 miles via truck. Two days later these cattle were processed in a conventional manner. As the steers came through the chute, every other calf was given 2 cc of the vaccine subcutaneously in the cervical region, the calves being identified by ear tag. The control calves were identified with an ear tag of a color different from the color of the tags identifying the injected calves. Both groups of calves were maintained on wheat pasture. The results of this evaluation are given below and clearly establish the efficacy and safety of the present vaccine under the conditions described.

TABLE I

| | Number Cattle | Number Affected by Bovine Shipping Fever | Number of Deaths |
|---|---|---|---|
| Control Cattle | 25 | 10 | 1 |
| Treated Cattle | 25 | 1 | 0 |

The statistical significance of the number of the untreated cattle which contracted shipping fever relative to the treated cattle is clear. The statistical significance of the untreated cattle which died due to shipping fever relative to the treated cattle is also clearly shown.

A field evaluation of the efficacy of the present vaccine prepared in accordance with the aforedescribed preparation included 1,300 head of cross bred steer and heifer calves weighing between 180 and 250 pounds which were shipped over 1,000 miles by truck after purchase. 500 Calves were purchased in June and lots of 400 calves each were purchased in July and August. All calves were processed according to conventional techniques and were vaccinated against Infectious Bovine Rhinotracheitis, Bovine Virus Diarrhea, Leptospirosis, and Clostridial Infections. All sick calves were treated with antibiotics and sulfonamides according to conventional techniques. The animals were maintained on good native pasture with free access to supplemental feed. The 500 calves purchased in June were not vaccinated with the composition matter described hereinabove. These 500 calves, therefore, serve as non-vaccinated controls. The calves received in July and August were vaccinated with the above-described vaccine. Over 150 of the calves received in June became sick with the typical symptoms of Shipping Fever Pneumonia and Shipping Fever Enteritis. Over 10% of the 500 control (unvaccinated) calves died in spite of vigorous conventional treatment. The 800 calves received in July and August had pasture and corral contact with the surviving controls. Only slightly over 30 of the July and August (vaccinated) calves became sufficiently sick to warrant treatment. Only seven of these 30 animals died. The following table summarizes these results:

TABLE II

| | Number of Head | Number Affected by Bovine Shipping Fever | Number of Deaths |
|---|---|---|---|
| Control Calves | 500 | 150 + (30%) | 50 + (10%) |
| Treated | 800 | 30 + (3.75%) | 7 (0.88%) |

TABLE II-continued

| | Number of Head | Number Affected by Bovine Shipping Fever | Number of Deaths |
|---|---|---|---|
| Calves | | | |

Although the example given relates to shipping fever prophylaxis in cattle, the same procedures can be followed in the preparation of a vaccine to treat other animal species including, but not limited to, sheep, horses, water buffalo, wild species of hooved animals, and other animal species. Vaccines prepared for a particular animal species utilize either all of the species of organisms responsible for shipping fever in that animal species to provide the killed organism in the vaccine, or a plurality of such species of the most important pathogenic organisms. As indicated previously, treatment of an animal with a vaccine according to the invention produces a significantly higher over-all resistance response level than would the separate administration of an individual bacterin or individual bacterins.

The foregoing is considered as illustrative on the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed as new is as follows:

1. A method for prophylactically and therapeutically treating livestock for selected specific disease entities that constitute either individually or in combination the bacterial phase of the shipping disease syndrome prior to exposure, during incubation, or during the symptomatic phase of the disease, which method comprises:
   administering to said livestock subcutaneously into the lymph drainage of the cervical region an effective amount of a water-in-oil emulsion having suspended in the aqueous phase thereof a mixture consisting essentially of the killed forms of *Pasteurella multocida*, *Pasteurella hemolytica*, and *Salmonella typhimurium*.

2. The method of claim 1 wherein said livestock comprises lambs.

3. The method of claim 1 wherein said livestock comprises calves.

4. The method of claim 1 wherein said emulsion has suspended additionally in the aqueous phase thereof a mixture including the killed forms of *Escherichia coli*, *Paracolon* species, *Proteus vulgaris*, *Pseudomonas aeruginosa*, and *Morexella bovis*.

* * * * *